United States Patent
Kim et al.

(10) Patent No.: US 10,624,769 B2
(45) Date of Patent: Apr. 21, 2020

(54) HYBRID STENT

(71) Applicants: CG BIO CO., LTD., Seongnam-si (KR); THE ASAN FOUNDATION, Seoul (KR)

(72) Inventors: Han Ki Kim, Seoul (KR); Hyun Seung Ryu, Yongin-si (KR); Jun Hyuk Seo, Seongnam-si (KR); Jun Kyu Park, Gwangju (JP); Seok Beom Song, Seongnam-si (KR); Chang Hun Kum, Seoul (KR); Jae Hwa Cho, Seoul (KR); Gyu Hyun Jin, Gwangju (KR); Deok Hee Lee, Seoul (KR); Seon Moon Hwang, Bucheon-si (KR); Tae Il Kim, Seoul (KR); Ok Kyun Lim, Seoul (KR); Ga Young Lee, Seoul (KR)

(73) Assignees: CG BIO CO., LTD., Gyeonggi-Do (KR); THE ASAN FOUNDATION, Seoul (KR)

( * ) Notice: Subject to any disclaimer, the term of this patent is extended or adjusted under 35 U.S.C. 154(b) by 28 days.

(21) Appl. No.: 15/574,330

(22) PCT Filed: Sep. 21, 2015

(86) PCT No.: PCT/KR2015/009900
§ 371 (c)(1),
(2) Date: Nov. 15, 2017

(87) PCT Pub. No.: WO2016/186262
PCT Pub. Date: Nov. 24, 2016

(65) Prior Publication Data
US 2018/0140443 A1    May 24, 2018

(30) Foreign Application Priority Data

May 15, 2015 (KR) .......................... 10-2015-0067832

(51) Int. Cl.
*A61F 2/88* (2006.01)
*A61F 2/91* (2013.01)
(Continued)

(52) U.S. Cl.
CPC ............... *A61F 2/88* (2013.01); *A61F 2/91* (2013.01); *A61F 2/07* (2013.01); *A61F 2002/828* (2013.01); *A61F 2230/0091* (2013.01)

(58) Field of Classification Search
CPC .... A61F 2/88; A61F 2/225; A61F 2/91; A61F 2/07; A61F 2002/828; A61F 2220/0058;
(Continued)

(56) References Cited

U.S. PATENT DOCUMENTS 6,042,597 A * 3/2000 Kveen .................. A61F 2/91
   623/1.15
6,610,086 B1 * 8/2003 Kock .................... A61F 2/91
   623/1.15
(Continued)

FOREIGN PATENT DOCUMENTS

JP        5695259       4/2015
KR     20030094286    12/2003
(Continued)

OTHER PUBLICATIONS

International Search Report—PCT/KR2015/009900 dated Feb. 16, 2016.

*Primary Examiner* — Paul B Prebilic
(74) *Attorney, Agent, or Firm* — Cantor Colburn LLP (57) ABSTRACT

A hybrid stent includes multiple main cells aligned in a spiral shape and including multiple first link units which are aligned diagonally and spaced at a predetermined distance from each other and multiple second link units which connect adjacent first link units among the multiple first link
(Continued)

units and are spaced at a predetermined distance from each other, and one or more open cells adjacent to the multiple main cells in a longitudinal direction and aligned in a spiral shape.

7 Claims, 6 Drawing Sheets

(51) Int. Cl.
*A61F 2/07* (2013.01)
*A61F 2/82* (2013.01)

(58) Field of Classification Search
CPC ........ A61F 2220/0091; A61F 2220/223; A61F 2250/001; A61F 2250/0048; A61F 2250/0028; A61F 2250/0037; A61F 2/885
USPC ....................................................... 623/1.22
See application file for complete search history.

(56) References Cited

U.S. PATENT DOCUMENTS

| | | | |
|---|---|---|---|
| 8,486,133 B2* | 7/2013 | Addonizio | A61F 2/91 623/1.15 |
| 2008/0097582 A1* | 4/2008 | Shanley | A61F 2/88 623/1.22 |
| 2009/0036976 A1* | 2/2009 | Beach | A61F 2/915 623/1.22 |
| 2013/0218254 A1* | 8/2013 | Cattaneo | A61F 2/82 623/1.2 |

FOREIGN PATENT DOCUMENTS

| | | |
|---|---|---|
| KR | 20120132368 | 12/2012 |
| KR | 20120138975 | 12/2012 |
| KR | 20140041547 | 4/2014 |
| KR | 20140140077 | 12/2014 |
| KR | 20150044114 | 4/2015 |

* cited by examiner

HYBRID STENT

TECHNICAL FIELD

The present disclosure relates to a hybrid stent.

BACKGROUND

A cerebrovascular disease, which typically causes a stroke, occurs suddenly and is accompanied by symptoms such as loss of consciousness, quadriplegia, and loss of speech. In many cases, the disease progresses rapidly in a short time. If one has a stroke, he/she is highly likely to die. Even if he/she does not die, it leaves him/her severely disabled. Therefore, he/she cannot lead a normal life in many cases. Also, the cerebrovascular disease is the second most common cause of death after cancer. It is reported that 75 per 100,000 people die of strokes and about 200 per 100,000 people a year suffer a stroke.

Cerebrovascular diseases are roughly classified into an obstructive cerebrovascular disease and a haemorrhagic cerebrovascular disease. The obstructive cerebrovascular disease refers to damage to the brain mainly due to occlusion of a cerebral artery caused by various reasons, and the haemorrhagic cerebrovascular disease refers to a cerebral haemorrhage caused by the rupture of a blood vessel in the brain.

A representative lesion that causes the haemorrhagic cerebrovascular disease among the above-described two kinds of cerebrovascular diseases is a cerebral aneurysm. If a cerebral aneurysm ruptures and progresses to subarachnoid hemorrhage, it may cause severe brain damage and lead to severe and even lead to death. Therefore, it is necessary to treat a cerebral aneurysm, which can rupture anytime, in advance in order to protect the life of a patient.

As a treatment method for cerebral aneurysm, direct surgery such as aneurysm neck ligation has been performed. The aneurysm neck ligation is direct craniotomy and has been most commonly performed for years. However, the direct surgery is painful to patients and highly limited in surgery site. In order to solve this problem, a minimally invasive treatment method called coil embolization of filling the inside of cerebral aneurysm using a platinum coil has been performed. However, when the coil embolization is performed, it is necessary to insert a stent formed as a metal mesh suitable for the shape of aneurysm neck in order for the coil not to poke out after the coil embolization. Actually, in many cases of cerebral aneurysm, the aneurysm neck is wide, which is referred to as a wide-neck aneurysm or giant-neck aneurysm. If such an aneurysm occurs, insertion of a stent is inevitable in order to suppress a coil for embolization not to poke out and to readily induce embolus of a cerebral aneurysm.

In order for a subsidiary stent for embolization to stably reach the affected area after being inserted into the body, the subsidiary stent needs to pass through a narrow and tortuous blood vessel of the brain. Also, in order for a coil inserted into a cerebral aneurysm not to deviate and to withstand blood pressure, the coil needs to have excellent properties such as flexibility and radial resistance.

Further, markers formed of a material having high radioopacity need to be attached to the beginning and the end, respectively, of the stent.

The marker precisely shows a position of the stent on the X-ray, so that an operator can deploy the stent at an accurate position and also easily manage the stent after the embolization.

Stents can be classified into vascular stents and non-vascular stents depending on a target in which a stent is used. The vascular stents can also be classified into a coronary artery stent used for cardiovascular stenosis, a peripheral vascular stent, and a cerebrovascular stent.

The background technology of the present disclosure is disclosed in Korean Patent Laid-open Publication No. 10-2012-0132368.

DISCLOSURE OF THE INVENTION

Problems to be Solved by the Invention

In view of the foregoing, the present disclosure provides a hybrid stent which is configured as a hybrid cell structure including main cells and open cells and thus improved in flexibility as compared with a conventional stent including closed cells only and also applicable to a complicated and tortuous blood vessel of the brain.

Further, the present disclosure provides a hybrid stent which can be recaptured by positioning a line connecting vertices in left and right directions of a main cell in the same direction as a longitudinal direction of the stent.

Furthermore, the present disclosure provides a hybrid stent which is improved in flexibility by setting an open cell to have a smaller width than a main cell.

Moreover, the present disclosure provides a hybrid stent which is improved in flexibility by increasing the number of main cells per open cell.

However, problems to be solved by the present disclosure are not limited to the above-described problems. There may be other problems to be solved by the present disclosure.

Means for Solving the Problems

As a technical means for solving the above-described technical problems, a hybrid stent according to an exemplary embodiment of the present disclosure includes multiple main cells aligned in a spiral shape and including multiple first link units which are aligned diagonally and spaced at a predetermined distance from each other and multiple second link units which connect adjacent first link units among the multiple first link units and are spaced at a predetermined distance from each other, and one or more open cells adjacent to the multiple main cells in a longitudinal direction and aligned in a spiral shape.

According to an exemplary embodiment of the present disclosure, the multiple open cells and the multiple main cells may be aligned sequentially in an alternate manner.

According to an exemplary embodiment of the present disclosure, the multiple main cells may be aligned slantly with respect to a longitudinal direction of the stent and extended in a spiral shape along a longitudinal direction.

According to an exemplary embodiment of the present disclosure, the multiple open cells may be aligned in order for an open cell to be adjacent to two or more of the multiple main cells.

According to an exemplary embodiment of the present disclosure, the open cell may have a smaller width than the main cell.

According to an exemplary embodiment of the present disclosure, one of the multiple main cells may be formed by two of the multiple first link units and two of the multiple second link units, and a line connecting vertices in left and right directions among four vertices in up and down directions and left and right directions of the one main cell may be at an angle of 45° or less to the longitudinal direction of the stent.

According to an exemplary embodiment of the present disclosure, at least one of the first link units and the second link units forming the one main cell may be formed into a wave curve.

According to an exemplary embodiment of the present disclosure, the wave curve may have an S-shape.

According to an exemplary embodiment of the present disclosure, the second link unit may be formed into a linear shape, and the multiple open cells may be formed adjacent to the second link unit.

According to an exemplary embodiment of the present disclosure, the first link unit may be formed into a wave curve, and the multiple open cells may be formed adjacent to the first link unit.

According to an exemplary embodiment of the present disclosure, one of the multiple main cells may be formed by two first link units facing each other among the multiple first link units and two second link units facing each other among the multiple second link units, and may have a tilted diamond shape.

According to an exemplary embodiment of the present disclosure, a hybrid stent is a stent having a cylindrical structure of which both ends are opened in a longitudinal direction, and includes: an open cell unit including one or more open cells; and a main cell unit including multiple main cells. The open cell unit and the main cell unit are aligned in an alternate manner along a spiral direction and thus provide the cylindrical structure.

According to an exemplary embodiment of the present disclosure, the main cell unit may include multiple main cells aligned side by side along a width direction of a spiral.

According to an exemplary embodiment of the present disclosure, the open cell unit includes one or more open cells aligned side by side along the width direction of the spiral, and the number of main cells aligned side by side along the width direction of the spiral may be greater than the number of one or more open cells aligned side by side along the width direction of the spiral.

According to an exemplary embodiment of the present disclosure, the open cell unit may be at least partially discontinuous with an open cell unit adjacent thereto along the longitudinal direction of the cylindrical structure.

The above-described means for solving the problems are provided by way of illustration only and should not be construed as liming the present disclosure. Besides the above-described exemplary embodiments, there may be additional exemplary embodiments described in the accompanying drawings and the detailed description.

Effects of the Invention

According to the above-described means for solving the problems, a stent is configured as a hybrid cell structure including main cells and open cells and thus improved in flexibility as compared with a conventional stent including closed cells only and also applicable to a complicated and tortuous blood vessel of the brain.

Further, according to the present disclosure, a stent can be recaptured by positioning a line connecting vertices in left and right directions of a main cell in the same direction as a longitudinal direction of the stent.

Furthermore, according to the present disclosure, a stent can be improved in flexibility by setting an open cell to have a smaller width than a main cell.

Moreover, according to the present disclosure, a stent can be improved in flexibility by increasing the number of main cells per open cell.

Further, the effects to be achieved by the present disclosure are not limited to the above-described effects. Although not described herein, other effects to be achieved by the present disclosure can be clearly understood by those skilled in the art from the following description.

BEST MODE FOR CARRYING OUT THE INVENTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Hereinafter, the present disclosure will be explained in detail with reference to the accompanying drawings.

A stent of the present disclosure can be applied to, for example, a cerebrovascular stent used for cerebrovascular disease or a coronary artery stent used for cardiovascular stenosis such as a heart attack or myocardial infarction. However, the stent of the present disclosure is not limited thereto and can be applied to various application fields.

Figure 1:
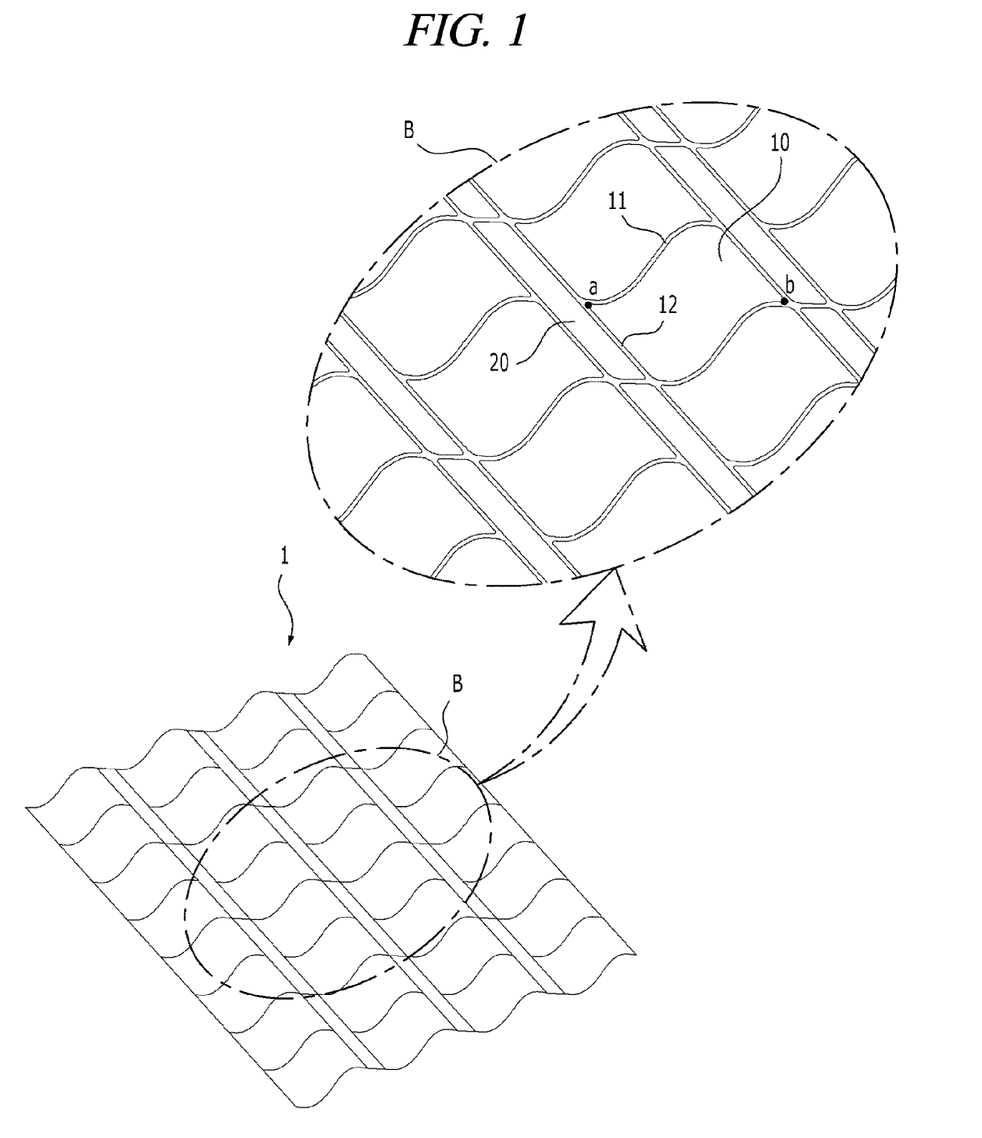
FIG. 1 is a diagram illustrating a forward hybrid stent according to an exemplary embodiment of the present disclosure.
Figure 2:
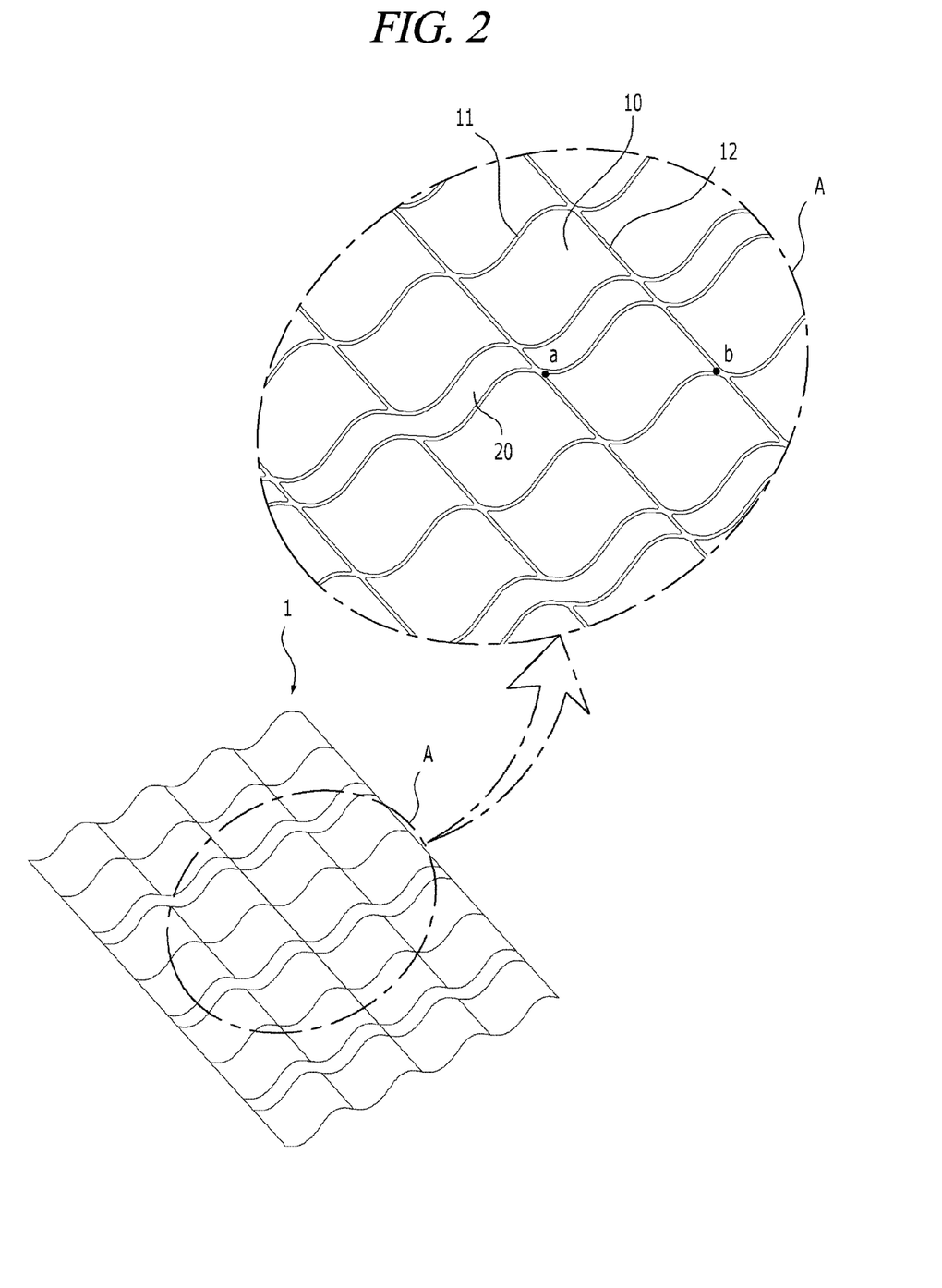
FIG. 2 is a diagram illustrating a backward hybrid stent according to an exemplary embodiment of the present disclosure.

FIG. 1 is a diagram illustrating a forward hybrid stent according to an exemplary embodiment of the present disclosure, and FIG. 2 is a diagram illustrating a backward hybrid stent according to an exemplary embodiment of the present disclosure.

According to an exemplary embodiment of the present disclosure, a hybrid stent 1 may have a cylindrical structure of which both ends are opened in a longitudinal direction. Further, in the hybrid stent 1, multiple main cells 10 and multiple open cells 20 may be aligned in an alternate manner.

The hybrid stent 1 can be classified as the forward hybrid stent 1 or the backward hybrid stent 1 depending on an alignment position of the open cell 20.

Furthermore, in the hybrid stent 1, the main cells 10 may be aligned in a spiral shape the open cells 20 configured to increase flexibility may be aligned between the main cells 10 aligned in the spiral shape. In this case, each open cell may be aligned corresponding to at least two main cells 10. As the number of main cells 10 corresponding to one open cell 20 is increased, the flexibility of the stent can be improved. In this case, the flexibility of the hybrid stent 1 can be adjusted by adjusting the number of main cells.

Also, the open cells 20 of the hybrid stent 1 may be aligned in the same manner as the main cells 10 aligned in a spiral direction.

Hereinafter, a structure of the hybrid stent 1 will be described in detail.

In the hybrid stent 1, the multiple main cells 10 and the multiple open cells 20 are aligned in a spiral shape. Thus, the hybrid stent 1 can have excellent flexibility and expansion force required for a stent.

The multiple main cells 10 may include multiple first link unit 11 which are aligned diagonally and spaced at a predetermined distance from each other. When the hybrid stent 1 is expanded, the multiple first link units 11 may be curved into a wave curve along a longitudinal direction of the hybrid stent 1. That is, the first link units 11 may be formed including peaks and valleys alternating each other.

Meanwhile, the multiple main cells 10 may include multiple second link unit 12 which connect adjacent first link units 11 among the multiple first link units 11 and are spaced at a predetermined distance from each other.

The multiple main cells 10 may be aligned slantly with respect to the longitudinal direction of the hybrid stent 1 as illustrated in FIG. 1 and FIG. 2. For example, the main cell 10 may be slantly formed at an angle of 30° to 60° with respect to the longitudinal direction of the hybrid stent 1.

Meanwhile, one of the multiple main cells 10 may be formed by two first link units 11 facing each other among the multiple first link units 11 and two second link units 12 facing each other among the multiple second link units 12. In this regard, one main cell 10 may have a tilted diamond shape.

Meanwhile, since the first link unit 11 and the second link unit 12 are connected adjacent to each other, one main cell 10 may have four vertices in approximately up and down directions and left and right directions, respectively. A line (not illustrated) connecting vertices a and b in the left and right directions among the four vertices may be at an angle of 45° or less to the longitudinal direction of the hybrid stent 1. That is, desirably, the line connecting the vertices a and b of the main cell 10 may be positioned in a recapture direction and thus can be recaptured.

Further, at least one of the first link units 11 and the second link units 12 forming the one main cell 10 may be formed into a wave curve. In this case, the wave curve may have an S-shape. For example, referring to FIG. 1, the first link unit 11 may be formed into a wave curve and the second link unit 12 may be formed into a linear shape.

For example, the multiple open cells 20 may be aligned sequentially in an alternate manner in a spiral shape along the longitudinal direction of the multiple main cells 10 and the hybrid stent 1. In this case, one open cell 20 may correspond to the multiple main cells 10. That is, the main cell can be understood as a closed cell and the open cell 10 can be understood as a cell having an area corresponding to multiple closed cells aligned side by side. The concepts of the closed cell and the open cell are obvious to those skilled in the art. Therefore, a more detailed explanation thereof will be omitted. Multiple series of elongate open cells 20 are aligned end-to-end in a spiral shape along and between two neighboring series of main closed cells 10.

As illustrated in FIG. 1 and FIG. 2, the open cell 20 may be formed to have a greater length and a smaller width than the main cell 10. Herein, referring to FIG. 1, the length of the open cell 20 may refer to a length in a progress direction of the spiral (11 to 5 o'clock directions in FIG. 1) and the width of the open cell 20 may refer to a width of the spiral.

In addition, a cavity of the open cell 20 may be formed smaller than a cavity of the main cell 10. Since the open cell 20 has a smaller cavity than the main cell 10, a higher flexibility than that of a conventional closed type (see the basic type in FIG. 3A) can be secured in the range in which a cerebrovascular stent can be recaptured.

Herein, as illustrated in FIG. 1 and FIG. 2, one of the multiple open cells 20 may be aligned adjacent to two or more main cells 10. Although FIG. 1 and FIG. 2 illustrate that one open cell 20 is aligned adjacent to two main cells 10, the number of main cells 10 is not limited.

Meanwhile, if the multiple open cells 20 are aligned at positions adjacent to the main cells 10, they may be aligned at various positions. That is, the open cell 20 may be aligned at a position adjacent to the second link unit 12 of the main cell 10 as illustrated in FIG. 1.

More specifically, the multiple open cells 20 may be aligned adjacent to the second link unit 12 formed into a linear shape as described above. The hybrid stent 1 configured as described above can be improved in a recapture function.

In another exemplary embodiment, the open cell 20 may be aligned at a position adjacent to the first link unit 11 of the main cell 10 as illustrated in FIG. 2.

More specifically, the multiple open cells 20 may be aligned adjacent to the first link unit formed into a wave curve as described above. The hybrid stent configured as described above can be improved in flexibility.

Hereinafter, various stents according to an exemplary embodiment of the present disclosure will be described by comparison with a conventional stent.

Figure 3A:
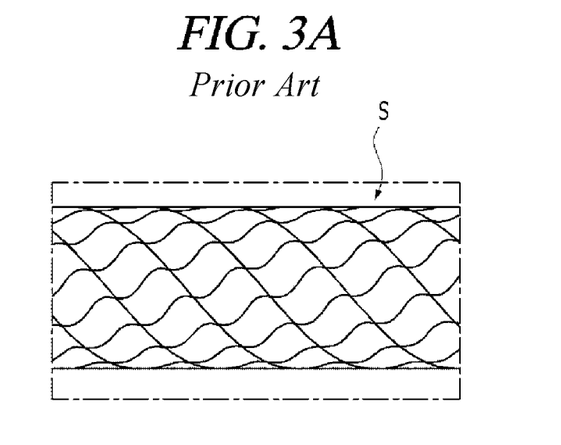
FIG. 3A is a diagram illustrating a conventional stent including closed main cells only.

FIG. 3A is a diagram illustrating a conventional stent including closed main cells only, and FIG. 3B to FIG. 3E are diagrams illustrating various stents according to an exemplary embodiment of the present disclosure.

The stent s illustrated in FIG. 3A is a conventional stent including the main cells 10 only. The stent s illustrated in FIG. 3A includes the closed main cells 10 only and thus has a remarkably lower flexibility than the hybrid stent 1 according to an exemplary embodiment of the present disclosure. In the following description, the stent illustrated in FIG. 3A is defined as a basic stent.

Figure 3B:
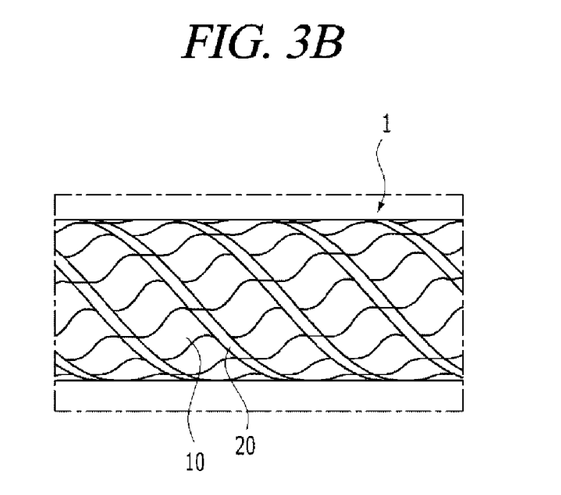
FIG. 3B to FIG. 3E are diagrams illustrating various stents according to an exemplary embodiment of the present disclosure.

FIG. 3B is a diagram illustrating the hybrid stent 1 according to an exemplary embodiment of the present disclosure in which one open cell 20 is aligned corresponding to two main cells 10. Further, in the hybrid stent 1 illustrated in FIG. 3B, the open cell 20 may be aligned adjacent to the second link unit 12 of the main cell 10, i.e., in the neighborhood of the second link unit 12. In the following description, the hybrid stent 1 illustrated in FIG. 3B will be defined as a first forward stent.

Figure 3C:
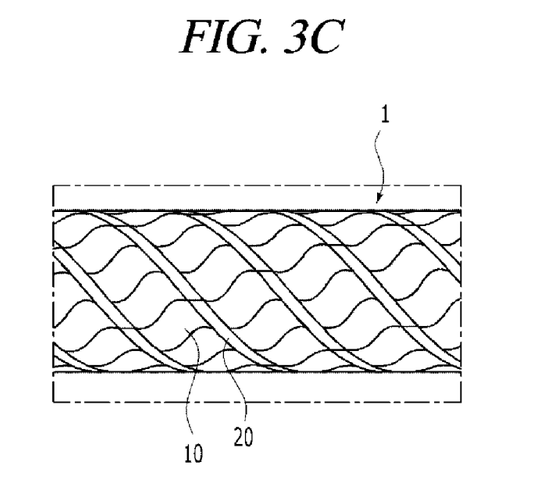

FIG. 3C is a diagram illustrating the stent 1 according to an exemplary embodiment of the present disclosure in which one open cell 20 is aligned corresponding to three main cells 10. Further, in the hybrid stent 1 illustrated in FIG. 3C, the open cell 20 may be aligned adjacent to the second link unit 12 of the main cell 10, i.e., in the neighborhood of the second link unit 12, like the hybrid stent 1 illustrated in FIG. 3B. In the following description, the hybrid stent 1 illustrated in FIG. 3C will be defined as a second forward stent.

Figure 3D:
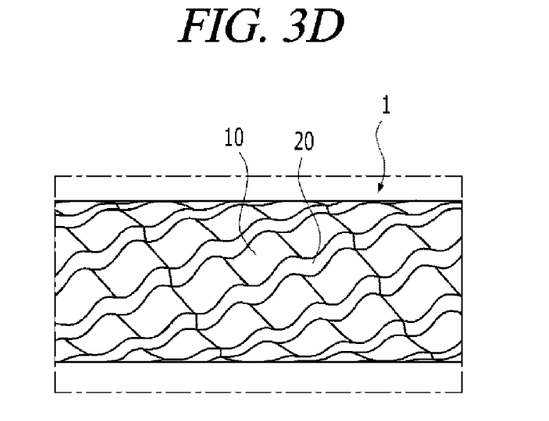

FIG. 3D is a diagram illustrating the hybrid stent 1 according to an exemplary embodiment of the present disclosure in which one open cell 20 is aligned corresponding to three main cells 10 and the open cell 20 may be aligned adjacent to the first link unit 11 of the main cell 10, i.e., in the neighborhood of the first link unit 11. In the following description, the hybrid stent 1 illustrated in FIG. 3D will be defined as a backward stent.

Figure 3E:
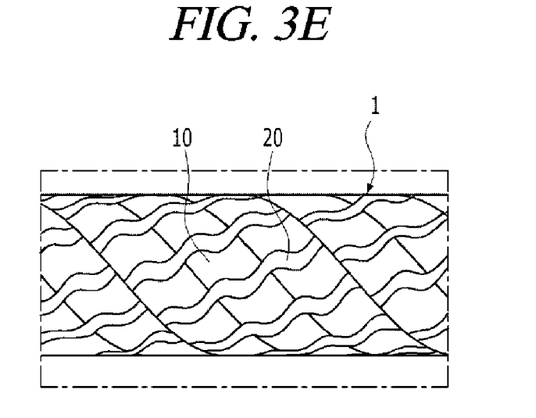

FIG. 3E is a diagram illustrating the hybrid stent 1 according to an exemplary embodiment of the present disclosure in which one open cell 20 is aligned corresponding to three main cells 10 and which is similar to the stent illustrated in FIG. 3D. However, in the stent illustrated in FIG. 3D, multiple open cells 20 are continuously formed into a spiral shape and multiple main cells 10 are formed into a spiral shape as being adjacent to the multiple open cells 20, whereas in the stent illustrated in FIG. 3E, one open cell 20 forms a part of a spiral shape and three main cells 10 form a part of the spiral shape as being adjacent to the one open cell 20. Thus, the stent illustrated in FIG. 3D and the stent illustrated in FIG. 3E are different in shape. In other words, in an exemplary embodiment of the stent illustrated in FIG. 3E, it can be seen that each open cell 20 is discontinuously formed as deviating from an open cell 20 adjacent thereto in a longitudinal direction of the stent and main cells 20 corresponding in number to the one open cell 20 (three in FIG. 3E) are continuously formed into a spiral shape.

Also, the hybrid stent 1 according to an exemplary embodiment of the present disclosure may be formed as a hybrid structure including a forward stent and a backward stent.

Meanwhile, Table 1 shows the result of performance comparison among the basic stent, the first forward stent, the second forward stent, and the backward stent.

TABLE 1

Figure 4:
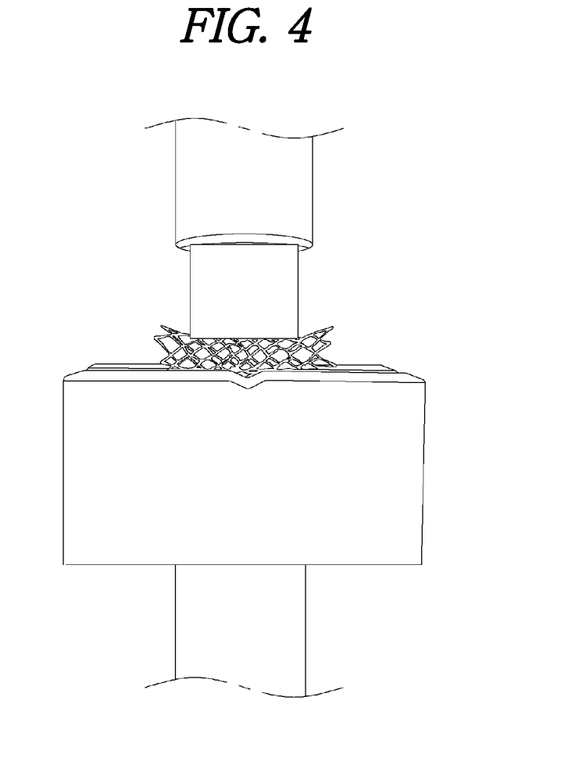
FIG. 4 show a test method of radial force for hybrid stents according to the present disclosure.
Figure 5:
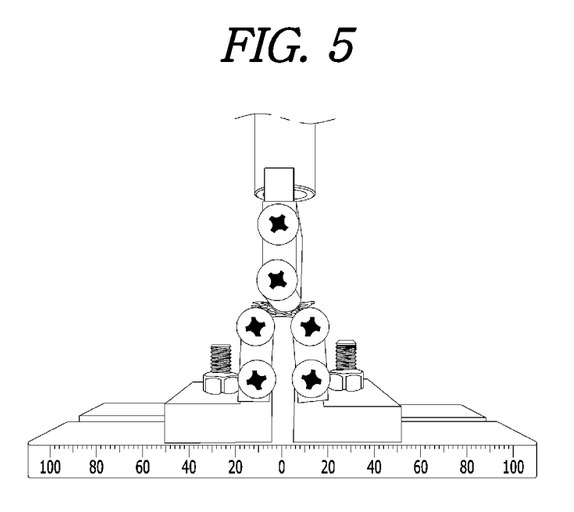
FIG. 5 show a test method of flexibility for hybrid stents according to the present disclosure.

|  | Radial force | Flexibility |
| --- | --- | --- |
| Testing method | FIG. 4 | FIG. 5 |
| Basic type | 1.380N | 0.250N |
| First forward type | 1.010N | 0.186N |
| Second forward type | 0.728N | 0.152N |
| Backward type | 0.966N | 0.174N |

As shown in Table 1, the first forward, second forward, and backward hybrid stents according to an exemplary embodiment of the present disclosure may be reduced in radial force and improved in flexibility as compared with the conventional basic stent.

Meanwhile, the hybrid stent 1 according to an exemplary embodiment of the present disclosure can be understood from the following point of view.

The hybrid stent 1 according to an exemplary embodiment of the present disclosure can be understood as including an open cell unit including one or more open cells 20 and a main cell unit including multiple main cells 10 in which the open cell unit and the main cell unit are aligned in an alternate manner along a spiral direction and thus provide the cylindrical structure.

For example, referring to an exemplary embodiment illustrated in FIG. 3D, the stent 1 illustrated in FIG. 3D may include an open cell unit including one open cell 20 and a main cell unit including three main cells 10 which are aligned in an alternate manner along a spiral direction.

Specifically, according to the above-described point of view, it has been described that in the stent 1 illustrated in FIG. 3D, multiple open cells 20 are formed into a spiral shape including only the open cells 20 along the 2 to 8 o'clock directions and multiple main cells 10 are formed into a spiral shape including only the main cells 10 along the 2 to 8 o'clock directions as being adjacent to the spiral shape of the multiple open cells 20 and the longitudinal direction of the stent. However, according to the present point of view, it can also be understood that the stent 1 illustrated in FIG. 3D has a spiral shape formed by aligning one open cell 20 (open cell unit) and three main cells 10 (main cell unit) in an alternate manner along the 11 to 5 o'clock directions.

That is, according to the above-described point of view, it can be understood that the hybrid stent 1 according to an exemplary embodiment of the present disclosure has a cylindrical structure formed by combining two spiral shapes (a spiral formed by main cells and a spiral formed by open cells), whereas according to the present point of view, it can be understood that the hybrid stent 1 according to an exemplary embodiment of the present disclosure has a cylindrical structure formed by only one spiral shape in which open cells and main cells are combined.

Further, it can also be understood that in the stent 1 according to an exemplary embodiment illustrated in FIG. 3E, an open cell unit including one open cell 20 and a main cell unit including three main cells 10 are aligned in an alternate manner along a spiral direction.

As illustrated in FIG. 3E, in the hybrid stent 1 according to an exemplary embodiment of the present disclosure, each open cell unit may be at least partially discontinuous with an open cell unit adjacent thereto along a longitudinal direction of the cylindrical structure. Specifically, as compared with the stent 1 according to the exemplary embodiment illustrated in FIG. 3D in which the open cell units are continuously connected to each other along a width direction of the spiral (2 to 8 o'clock directions in FIG. 3D), in the stent 1 illustrated in FIG. 3E, the open cell units are not continuously connected to each other along a width direction of the spiral (2 to 8 o'clock directions in FIG. 3E) but entirely (or partially) deviate from each other.

The present point of view can also be understood from the stent 1 according to the exemplary embodiments illustrated in FIG. 3B and FIG. 3C. Specifically, the stent 1 illustrated in FIG. 3B may have a cylindrical structure with a spiral shape formed by aligning one open cell 20 (open cell unit) and two main cells 10 (main cell unit) in an alternate manner along the 2 to 8 o'clock directions. Also, the stent 1 illustrated in FIG. 3C may have a cylindrical structure with a spiral shape formed by aligning one open cell 20 (open cell unit) and three main cells 10 (main cell unit) in an alternate manner along the 2 to 8 o'clock directions.

Further, referring to FIG. 3B to FIG. 3E, a main cell unit may include multiple main cells aligned side by side along a width direction of a spiral. Specifically, in FIG. 3B, two main cells are aligned side by side along a width direction of a spiral (11 to 5 o'clock directions) and in FIG. 3C, three main cells are aligned side by side along a width direction of a spiral (11 to 5 o'clock directions). Also, in FIG. 3D and FIG. 3E, three main cells are aligned side by side along a width direction of a spiral (2 to 8 o'clock directions).

Also, an open cell unit may include one or more open cells aligned side by side along the width direction of the spiral. Although FIG. 3B to FIG. 3E illustrate that one open cell is aligned, multiple open cells may be aligned side by side along the width direction of the spiral. However, desirably, the number of open cells aligned side by side along the width direction of the spiral may be set to be smaller than the number of main cells aligned side by side along the width direction of the spiral considering the concepts of an open cell and a main cell (closed cell).

As described above, the hybrid stent 1 according to an exemplary embodiment of the present disclosure has excellent flexibility and thus can be applied to a complicated and tortuous blood vessel of the brain, and also has a stent structure which can be recaptured to be adjusted in position during a treatment and thus is optimized for a blood vessel of the brain.

However, as described above, application fields of the stent of the present disclosure are not limited thereto. For example, the stent of the present disclosure can be applied to a cerebrovascular stent used for cerebrovascular disease and a coronary artery stent used for cardiovascular stenosis such as a heart attack or myocardial infarction. Also, the stent of the present disclosure can be applied to various application fields and similar fields relevant to a stent in addition to the above-described cerebrovascular stent and coronary artery stent.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A hybrid stent having a cylindrical structure of which both ends are opened in a longitudinal direction, the hybrid stent comprising:
    multiple series of main closed cells in which each series of main closed cells are consecutively aligned in a spiral shape along a longitudinal direction of the hybrid stent and slantly aligned at an angle of 45 degrees or less with respect to the longitudinal direction;
    multiple first link units which are aligned slantly with respect to the longitudinal direction and spaced at a predetermined distance from each other, and multiple pairs of second link units in which each pair of second link units is aligned along and between two neighboring series of main closed cells and connects two neighboring first link units, wherein each main closed cell is defined by two neighboring first link units and two neighboring second link units; and
    multiple series of elongate open cells in which each series of open cells are aligned end-to-end in a spiral shape along and between two neighboring series of main closed cells in the longitudinal direction, wherein each open cell is defined by each pair of second link units and two neighboring first link units, and each open cell is defined to correspond to two or more neighboring main closed cells.

2. The hybrid stent of claim 1, wherein the multiple series of open cells and the multiple series of main closed cells are aligned sequentially in an alternate manner.

3. The hybrid stent of claim 1, wherein the each open cell has a width smaller than that of the each main closed cell.

4. The hybrid stent of claim 1, wherein the multiple first link units are formed to have a wave curve, or the multiple second link units are formed to have a wave curve.

5. The hybrid stent of claim 4, wherein the wave curve has an S-shape.

6. The hybrid stent of claim 1, wherein the multiple second link units are formed in a linear shape.

7. The hybrid stent of claim 1, wherein the each main closed cell has a tilted diamond shape.

* * * * *

UNITED STATES PATENT AND TRADEMARK OFFICE
CERTIFICATE OF CORRECTION

PATENT NO. : 10,624,769 B2
APPLICATION NO. : 15/574330
DATED : April 21, 2020
INVENTOR(S) : Han Ki Kim et al.

Page 1 of 1

It is certified that error appears in the above-identified patent and that said Letters Patent is hereby corrected as shown below:

On the Title Page

Item (72) Inventors:
Please correct the nationality of fourth inventor, Jun Kyu PARK from JP to KR.

Signed and Sealed this
First Day of September, 2020

Andrei Iancu
*Director of the United States Patent and Trademark Office*